(12) United States Patent
Bretthauer (10) Patent No.: US 11,353,431 B2
(45) Date of Patent: Jun. 7, 2022

(54) PHOTOACOUSTIC SENSOR

(71) Applicant: Infineon Technologies AG, Neubiberg (DE)

(72) Inventor: Christian Bretthauer, Munich (DE)

(73) Assignee: INFINEON TECHNOLOGIES AG, Neubiberg (DE)

(*) Notice: Subject to any disclaimer, the term of this patent is extended or adjusted under 35 U.S.C. 154(b) by 90 days.

(21) Appl. No.: 16/706,134

(22) Filed: Dec. 6, 2019

(65) Prior Publication Data

US 2020/0256833 A1    Aug. 13, 2020

(30) Foreign Application Priority Data

Feb. 11, 2019  (EP) ..................................... 19156437

(51) Int. Cl.
*G01N 29/24*  (2006.01)
*G01N 15/06*  (2006.01)
(Continued)

(52) U.S. Cl.
CPC ......... *G01N 29/2418* (2013.01); *G01N 15/06* (2013.01); *G01N 33/0037* (2013.01);
(Continued)

(58) Field of Classification Search
CPC ........... G01N 29/2418; G01N 29/2425; G01N 15/06; G01N 33/0037; G01N 2015/0046;
(Continued)

(56) References Cited

U.S. PATENT DOCUMENTS

| 4,817,413 A | 4/1989 | Asano et al. |
| 2009/0235720 A1* | 9/2009 | Smith ................ G01N 21/3504 73/31.05 |

(Continued)

FOREIGN PATENT DOCUMENTS

WO    2007054751 A1    5/2007

OTHER PUBLICATIONS

Haisch, Christoph. "Photoacoustic Analyzer for the Artifact-Free Parallel Detection of Soot and NO2 in Engine Exhaust". Analystical Chemistry and Institute of Hydrochemistry. pp. 7292-7296. Published Aug. 8, 2012 (Year: 2012).*

(Continued)

*Primary Examiner* — Tarun Sinha
(74) *Attorney, Agent, or Firm* — Slater Matsil, LLP (57) ABSTRACT

A photoacoustic sensor comprises an emitter for emitting electromagnetic radiation at a first wavelength and electromagnetic radiation at a second wavelength, wherein the first wavelength is for photoacoustically detecting particulate matter in a measurement cavity and the second wavelength is for photoacoustically detecting the particulate matter and at least one target gas in the measurement cavity. The photoacoustic sensor further comprises an acoustic transducer for transducing a first acoustic signal into a first sensor signal depending on an interaction of the electromagnetic radiation at the first wavelength and the particulate matter, and for transducing a second acoustic signal into a second sensor signal depending on an interaction of the electromagnetic radiation at the second wavelength with the particulate matter and the at least one target gas.

13 Claims, 5 Drawing Sheets

(51) Int. Cl.
*G01N 33/00* (2006.01)
*G01N 15/00* (2006.01)

(52) U.S. Cl.
CPC ........... *G01N 2015/0046* (2013.01); *G01N 2015/0693* (2013.01)

(58) Field of Classification Search
CPC .......... G01N 2015/0693; G01N 21/03; G01N 21/1702; G01N 21/33; G01N 21/3504
USPC ......................................................... 73/24.02
See application file for complete search history.

(56) References Cited

U.S. PATENT DOCUMENTS

| | | | |
|---|---|---|---|
| 2010/0107732 A1 | 5/2010 | Miklos et al. | |
| 2011/0019193 A1* | 1/2011 | Danno | G01N 21/39 356/433 |
| 2011/0290026 A1* | 12/2011 | Rice | G01N 21/39 73/602 |
| 2016/0216154 A1* | 7/2016 | Hofmeister | G01J 3/0286 |
| 2020/0056998 A1* | 2/2020 | Rusanov | G01N 21/71 |
| 2020/0271561 A1* | 8/2020 | Lavrovsky | B01D 35/1435 |
| 2021/0025742 A1* | 1/2021 | Toda | G01P 5/26 |

OTHER PUBLICATIONS

Faxvog, Fred R., et al., "Optoacoustic measurements of diesel particulate emissions", Journal of Applied Physics, 50, 7880, Jul. 29, 2008, 4 pages.

Haisch, Christoph et al., "Photoacoustic for the Artifact-Free Parallel Detection of Soot and NO2 in Engine Exhaust", Analytical Chemistry, pbs.acs.org/ac, Anal. Chem., 84, Aug. 8, 2012, pp. 7292-7296.

Jiang, Yalong et al., "Photoacoustic Compound Fire Alarm System for Detecting Particles and Carbon Monoxide in Smoke", Fire Technology, 52:5, Jan. 2016, 16 pages.

Yu, Zhenhong et al., "Differential photoacoustic spectroscopic (DPAS)-based technique for PM optical absorption measurements in the presence of light absorbing gaseous species", Aerosol Science and Technology, 51:12, Taylor & Francis, DOI: 10.1080/02786826.2017-1363866, Sep. 12, 2017, 12 pages.

Yu, Zhenhong et al., "A single-pass RGB differential photoacoustic spectrometer (RGB-DPAS) for aerosol absorption measurement at 473, 532, 671 nm", Aerosol Science and Technology, 53:1, Taylor & Francis, ISSN: 0278-6826, www.tandfonline.com/loi/uast20, DOI: 10.1080/02786826.2018.1551611, Dec. 20, 2018, 14 pages.

* cited by examiner

|  | CO2 | NO2 | PM (soot) |
|---|---|---|---|
| Wavelength [μm] | 4.2 | best between 360-420nm, cheap LDs e.g. for 405 and 450nm | any, but 805nm lowest cross sensitivity to gases |
| Absorption crossection (integral over band) [1/(m*ppm)] or [m^2/g] | 1.94E-03 | 1.6e-3 at 445nm | 10-20 depending on composition of PM |
| Expected min. concentration [ppm] or [μg/m^3] | 10 | 0.01 | 5 |
| Optical input power [mW] (integral over absorption band) | 0.2 | 150 (405nm+-5nm LD) | 500 (805nm+-10 LD) |
| Light source efficiency [%] | #VALUE! | 22.18% | 40.49% |
| Signal min. (cmin_abs[1/m]*Popt[mW]) | 0.004 | 0.0024 | 0.0375 |
| major noise sources | 1/f + ambient | white + ambient | white + ambient |
| Mic. Sensitivity (normalized) | 1 | e.g. resonant mode Q~6 | e.g. resonant mode Q~6 |

PHOTOACOUSTIC SENSOR

This application claims the benefit of European Application No. 19156437, filed on Feb. 11, 2019, which application is hereby incorporated herein by reference.

TECHNICAL FIELD

Embodiments of the present disclosure relate to a photoacoustic sensor for mutually sensing a target gas and particulate matter, and in particular a miniaturized photoacoustic $NO_2$ and fine particulate sensor module.

BACKGROUND

All over the world air pollution is a big problem. Air quality may be measured by means of the so-called Air Quality Index (AQI). For example, Europe has gained high media attention due to the "Dieselgate" scandal which led to an increasing awareness about $NO_2$ and fine particulate matter (PM) contamination. Thus, there is nowadays an increasing desire to monitor the major contaminants from combustion processes like $NO_2$ and PM by small, precise and cost effective sensors.

Generally, there is an interest to measure current air quality by sensing air contaminants, preferably being related with the AQI, such as for example one or more target gases and fine particulate matter.

Most of today's gas sensors rely on chemical adsorption processes on metal oxides which are by their chemical principle prone to aging and sensor drifts and sometimes also suffer from a lack of selectiveness. Their advantage is, however, that it is possible to realize very small form factors. Physical sensor principles like nondispersive infra-red (NDIR) or photoacoustic sensors (PAS) are usually a little larger than chemical sensors but in principle less prone to drift and aging issues, whereby the PAS concept promises at least smaller form factors than NDIR. For example physical sensors may be preferably used for sensing $CO_2$ as a target gas, wherein sensor modules using the PAS concept promises smaller form factors than NDIR.

Regarding detection of particulate matter (PM), the US Environmental Protection Agency (EPA) introduced the so-called National Air Quality-Standard for Particulate Matter, also referred to as the PM-Standard. As far as notations like PM10, PM2.5, PM1, PM0.3 and others are described herein, it is referred to the above mentioned National Air Quality-Standard for Particulate Matter.

Most of today's sensors for detecting particulate matter (PM) are based on light scattering which works fine for standards PM10, PM2.5 and partially also for PM1 but gets increasingly difficult for smaller particles and is not selective in terms of PM chemistry, e.g., water droplets and salt crystals are detected as false positives. The form factor is nowadays dominated by the fan of these sensors, as for large PM values like PM10 or PM2.5 a big volume of air has to be sampled in order to determine a meaningful value. For decreasing PM definitions like PM1 the number of particles per air volume increases and smaller air volumes may be sufficient but as said, capturing these small particles by light scattering becomes increasingly difficult.

A solution for measuring small soot particles of 300 nm and less is therefore highly desirable, as these particles are considered as being particularly harmful and a lowering of the PM standard to PM0.3 in the next few years is also not unlikely. Furthermore, it is desirable to have a sensor at hand which provides for mutually sensing particulate matter and at least one target gas based on a physical sensing principle.

Thus, a photoacoustic sensor according to claim 1 is suggested.

SUMMARY

The photoacoustic sensor according to the present disclosure comprises, inter alia, an emitter for emitting electromagnetic radiation at a first wavelength and electromagnetic radiation at a second wavelength, wherein the first wavelength is for photoacoustically detecting particulate matter in a measurement cavity and the second wavelength is for photoacoustically detecting the particulate matter and at least one target gas in the measurement cavity. The photoacoustic sensor further comprises an acoustic transducer for transducing a first acoustic signal into a first sensor signal depending on an interaction of the electromagnetic radiation at the first wavelength and the particulate matter, and for transducing a second acoustic signal into a second sensor signal depending on an interaction of the electromagnetic radiation at the second wavelength with the particulate matter and the at least one target gas.

BRIEF DESCRIPTION OF THE DRAWINGS

In the following, embodiments of the present disclosure are described in more detail with reference to the figures, in which.

DETAILED DESCRIPTION OF ILLUSTRATIVE EMBODIMENTS

Equal or equivalent elements or elements with equal or equivalent functionality are denoted in the following description by equal or equivalent reference numerals.

The at least one target gas to be detected by means of the photoacoustic sensor may be described by exemplarily referring to gases belonging to the family of nitrogen oxides, and particularly with exemplary reference to nitrogen dioxide $NO_2$. However, it is to be understood that these gases are only mentioned as non-limiting examples and gases other than those gases mentioned herein may be used as the at least one target gas.

Figure 1:
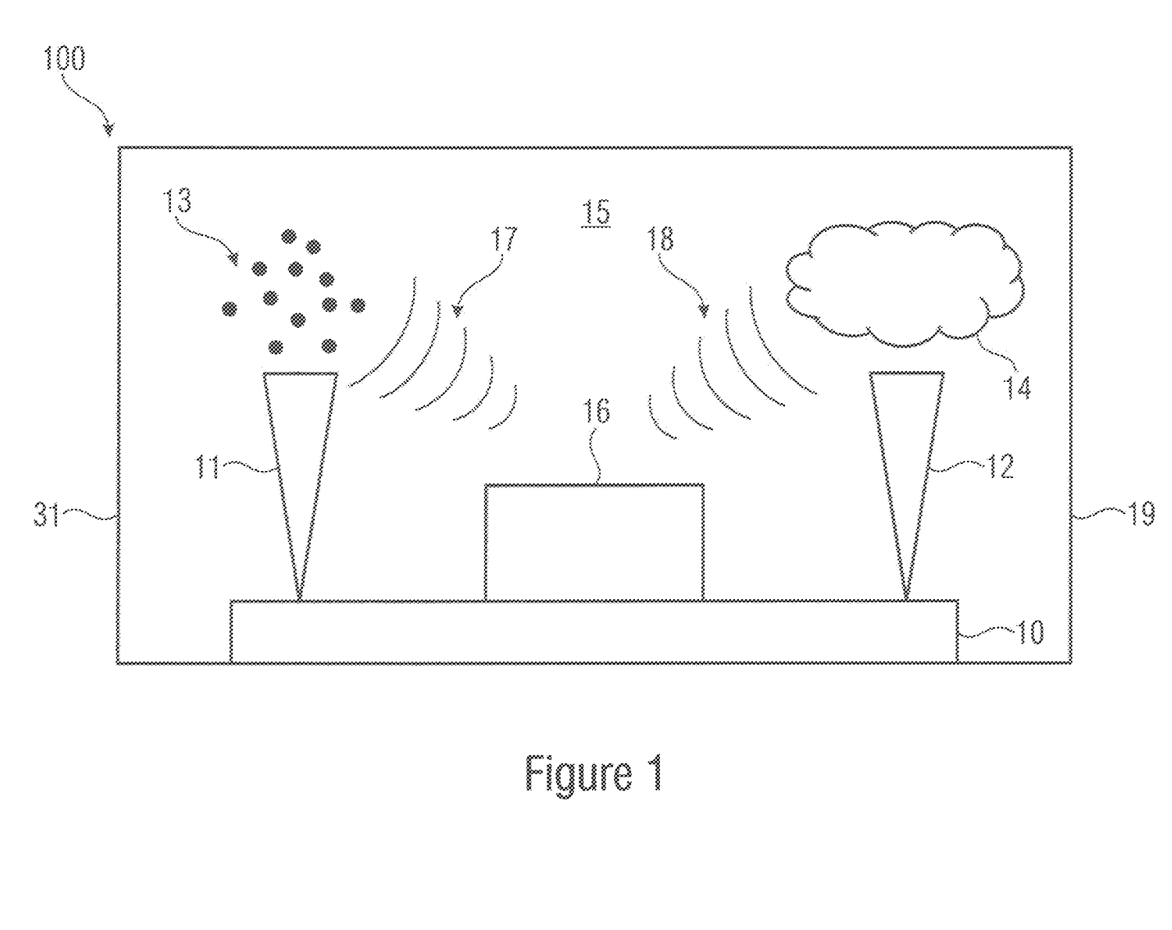
FIG. 1 shows a schematic side view of a photoacoustic sensor according to an embodiment.

FIG. 1 shows a first example of a photoacoustic sensor 100 according to the present disclosure.

The photoacoustic sensor 100 comprises an emitter 10 for emitting electromagnetic radiation 11 at a first wavelength and electromagnetic radiation 12 at a second wavelength. The electromagnetic radiation 11, 12 may be light comprising at least one of the visible spectrum, infrared spectrum and ultraviolet spectrum.

The first wavelength is for photoacoustically detecting particulate matter 13 in a measurement cavity 15 and the second wavelength is for photoacoustically detecting the particulate matter 13 and additionally at least one target gas 14 in the measurement cavity 15. The measurement cavity 15 may be part of the photoacoustic sensor 100, i.e., the photoacoustic sensor 100 may comprise the measurement cavity 15. The measurement cavity 15 may be defined by a housing 31 of the photoacoustic sensor 100.

The photoacoustic sensor 100 further comprises an acoustic transducer 16. The acoustic transducer 16 may, for instance, comprise a microphone and in particular a MEMS microphone (MEMS: Micro Electro Mechanical System). The acoustic transducer 16 is configured for transducing a first acoustic signal 17 into a first sensor signal, according to the photoacoustic principle, depending on an interaction of the electromagnetic radiation 11 at the first wavelength and the particulate matter 13. Furthermore, the acoustic transducer 16 is configured for transducing a second acoustic signal 18 into a second sensor signal, according to the photoacoustic principle, depending on an interaction of the electromagnetic radiation 12 at the second wavelength with the particulate matter 13 and additionally the at least one target gas 14.

According to the photoacoustic principle, the electromagnetic radiation 11 at the first wavelength may interact with the particulate matter 13 inside the measurement cavity 15, wherein the particulate matter 13 may absorb the electromagnetic radiation 11 at the first wavelength at least partially. The electromagnetic radiation 12 at the second wavelength may interact with the at least one target gas 14 inside the measurement cavity 15, wherein the at least one target gas 14 may absorb the electromagnetic radiation 12 at the second wavelength at least partially.

Each of the particulate matter 13 and the at least one target gas 14 may comprise a characteristic absorption spectrum, wherein the particulate matter 13 and the at least one target gas 14 may absorb different amounts of the respective electromagnetic radiation 11, 12 at different wavelengths. These characteristic absorption spectrums may also be referred to as fingerprints. Accordingly, the particulate matter 13 may comprise a different fingerprint than the at least one target gas 14 because the particulate matter 13 and the at least one target gas 14 may absorb different amounts of the electromagnetic radiation 11, 12 at different wavelengths.

According to an exemplary embodiment, the at least one target gas 14 may be a gas belonging to the family of nitrogen oxides. For instance, the at least one target gas 14 may be nitrogen dioxide $NO_2$ which may be of increased interest nowadays when examining the air quality. The particulate matter 13 may comprise one or more of soot, ashes and dust which may also be of increased interest nowadays when examining the air quality.

The particulate matter 13 may primarily comprise dark particles leading to a characteristic fingerprint according to which electromagnetic radiation in general may be absorbed over a wide spectrum. The above mentioned family of nitrogen oxides instead may comprise a characteristic fingerprint according to which electromagnetic radiation may preferably be absorbed in a range between 200 nm and 600 nm.

According to some exemplary embodiments, the emitter 10 may be configured to emit the electromagnetic radiation 12 at the second wavelength, wherein the second wavelength is in a range between 200 nm and 600 nm. More particular, the emitter 10 may be configured to emit the electromagnetic radiation 12 at the second wavelength, wherein the second wavelength is 405 nm±5 nm or 450 nm±5 nm, which may be preferable for detecting nitrogen oxides, such as $NO_2$.

According to some further exemplary embodiments, the emitter 10 may be configured to emit the electromagnetic radiation 11 at the first wavelength, wherein the first wavelength is in a range between 600 nm and 1100 nm, and more particularly the emitter 10 may be configured to emit the electromagnetic radiation 11 at the first wavelength, wherein the first wavelength is 805 nm±10 nm or 850 nm±10 nm. These ranges of the first wavelength may be preferable since the particulate matter 13 may absorb the electromagnetic radiation 11 at these ranges of the first wavelength while absorption of the electromagnetic radiation 11 at these ranges of the first wavelength by the at least one target gas 14 is comparably lower. In other words, absorption by the particulate matter 13 is comparably higher than absorption by the at least one target gas 14. Accordingly, emitting the electromagnetic radiation 11 at the above mentioned ranges of the first wavelength may help to avoid interference with the at least one target gas 14.

Generally, the first wavelength of the electromagnetic radiation 11 for detecting the particulate matter 13 is preferably to be chosen such that said first wavelength is different from the second wavelength of the electromagnetic radiation 12 for detecting the at least one target gas 14. It may be preferable to provide a band gap between the first and second wavelengths. Said band gap may be selected such that the at least one target gas 14 may be detectable by means of the second wavelength without interference by the first wavelength. For example, the first wavelength may be selected such that it lies outside the absorption spectrum of the at least one target gas 14.

Due to the above mentioned absorption of the electromagnetic radiation 11, 12 by the particulate matter 13 and the at least one target gas 14, respectively, the temperature inside the measurement cavity 15 increases. The emitter 10 may be configured to emit the electromagnetic radiation 11, 12 intermittently, and therefore the temperature inside the measurement cavity 15 correspondingly increases and decreases intermittently. This effect may cause an acoustic signal, e.g., an acoustic wave, inside the measurement cavity 15 which may be detected by the acoustic transducer 16.

The absorption of the electromagnetic radiation 11 at the first wavelength by the particulate matter 13 may generate the first acoustic signal 17, wherein the first acoustic signal 17 is different from the second acoustic signal 18 generated by the absorption of the electromagnetic radiation 12 at the second wavelength by the at least one target gas 14.

Figure 2:
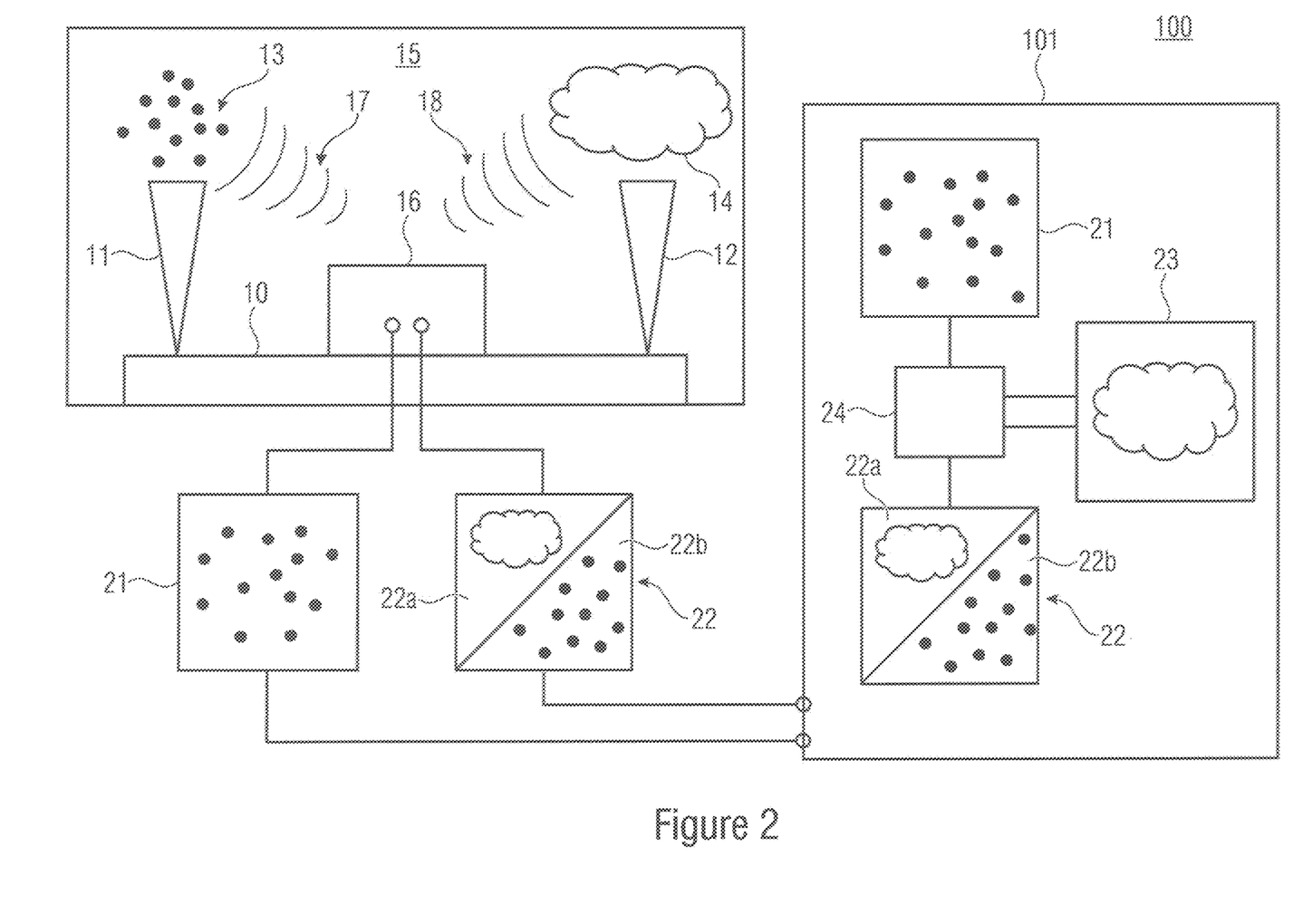
FIG. 2 shows a schematic side view of a photoacoustic sensor according to an embodiment.

As can be seen in FIG. 2, the acoustic transducer 16 may transduce the first acoustic signal 17 generated by the particulate matter 13 into a first sensor signal 21, and the acoustic transducer 16 may transduce the second acoustic signal 18 generated by the at least one target gas 14 into a second sensor signal 22.

However, as mentioned above, the particulate matter 13 may absorb over a wide spectrum. For example, the particulate matter 13 may also absorb, at least partially, the electromagnetic radiation 12 at the second wavelength. Accordingly, the second acoustic signal 18 may be generated not only by the at least one target gas 14 but also, at least partially, by the particulate matter 13. Thus, the second acoustic signal 18 may comprise a first portion being related with the at least one target gas 14 and a second portion being related with the particulate matter 13. Accordingly, the second sensor signal 22 may also comprise a first sensor signal portion 22a being related with the at least one target gas 14 and a second sensor signal portion 22b being related with the particulate matter 13.

In order to determine the quantity of the particulate matter 13 and the at least one target gas 14 inside the measurement cavity 15, a controller 101 may be provided. The controller 101 may be configured to determine a quantity of the particulate matter 13 inside the measurement cavity 15 based on the first sensor signal 21 and to determine a mutual quantity of the particulate matter 13 and the at least one target gas 14 inside the measurement cavity 15 based on the second sensor signal 22.

The controller 100 may be configured to improve the measurement of the quantity of the at least one target gas 14 by minimizing or even deleting the second sensor signal portion 22b being related with the particulate matter 13 from the second sensor signal 22. For example, the controller 100 may comprise a combining module 24 for combining the first sensor signal 21 and the second sensor signal 22. For example, the combining module 24 may be configured to combine the sensor signals 21, 22 by subtracting the second sensor signal portion 22b of the second sensor signal 22 from the first sensor signal 21 such that the third sensor signal 23 would be a differential signal. In result, the controller 100 or the combining module 101 may generate a third sensor signal 23 being related with the at least one target gas 14 and in which the amount of the particulate matter 13 (i.e., the second sensor signal portion 22b) may be reduced or even deleted.

The first sensor signal 21 and the second sensor signal portion 22b of the second sensor signal 22 may be identical. In this case, the second sensor signal portion 22b representing the fraction of the particulate matter 13 may be completely removed from the third sensor signal 23 such that the third sensor signal 23 may represent the quantity of the at least one target gas 14 only. This may make the measurement of the at least one target gas 14 more precise and robust against PM cross-sensitivity.

Accordingly, the controller boo may be configured to determine a quantity of the at least one target gas 14 inside the measurement cavity 15 based on a combination of the first and second sensor signals 21, 22.

In the non-limiting examples shown in FIGS. 1 and 2, the acoustic transducer 16 is arranged on the emitter 10. Alternatively, the acoustic transducer 16 may be arranged separately from, e.g., next to, the emitter 10.

Figure 3:
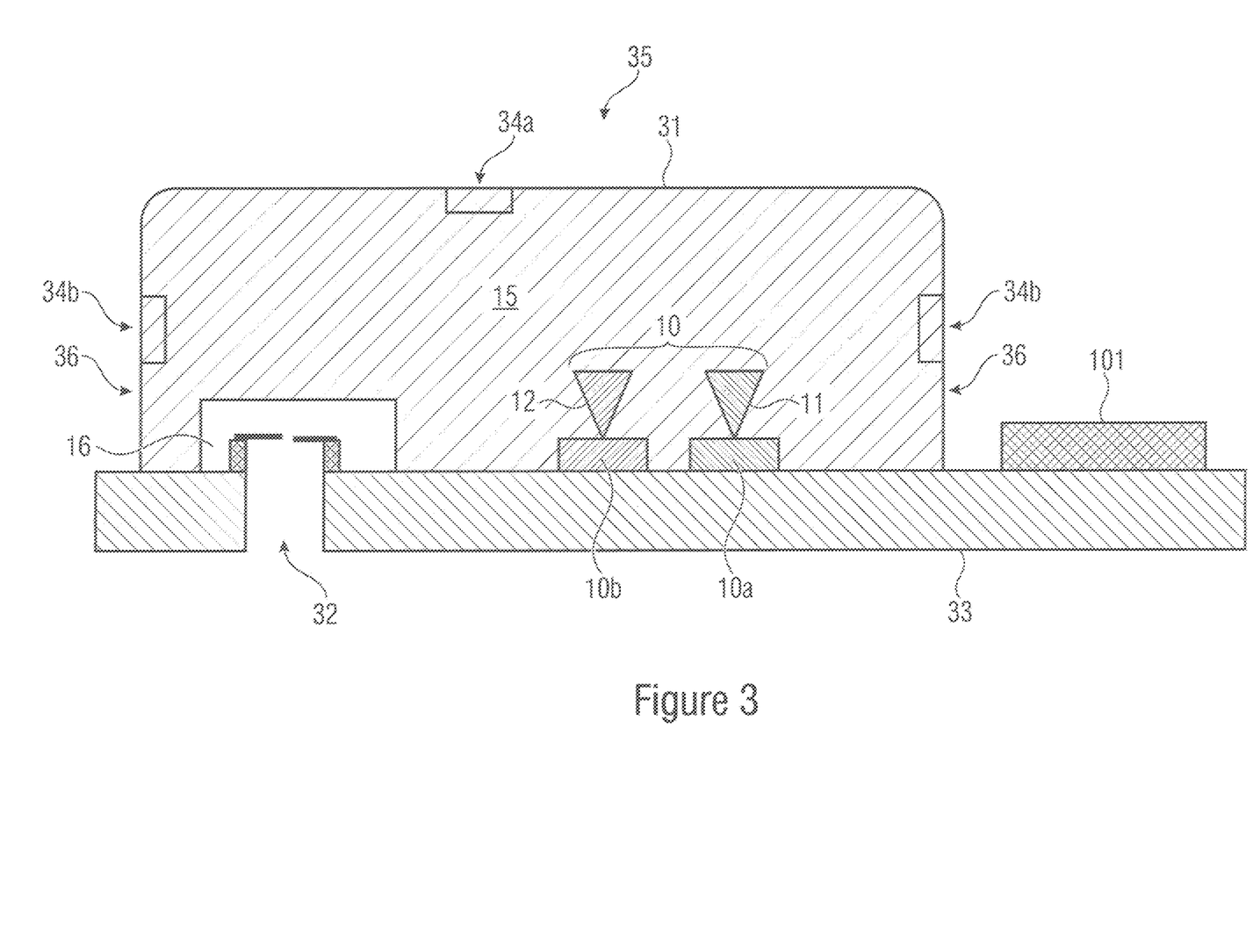
FIG. 3 shows a schematic side view of a photoacoustic sensor according to an embodiment.

FIG. 3 shows a further exemplary embodiment of a photoacoustic sensor boo according to the present disclosure. The emitter 10 may comprise a first emitter element boa for emitting the electromagnetic radiation 11 at the first wavelength and a second emitter element bob for emitting the electromagnetic radiation 12 at the second wavelength. Optionally, at least one of the first and second emitter elements boa, bob may be tunable through a wavelength spectrum covering at least one of the first and second wavelengths.

Alternatively, the emitter 10 may comprise only one source of electromagnetic radiation being tunable through a wavelength spectrum covering the first and second wavelengths.

The emitter 10 may comprise at least one of a Light Emitting Diode (LED) and a Laser Diode (LD). For example, the emitter boa may comprise a first LED or LD boa being configured to emit the electromagnetic radiation 11 at the first wavelength. Additionally or alternatively, the emitter 10 may comprise a second LED or LD 10b being configured to emit the electromagnetic radiation 12 at the second wavelength. For example, the first emitter element boa may be a red LED or LD and the second emitter element 10b may be a blue LED or LD.

These variants of providing LEDs or LDs are preferable over common photoacoustic sensors using infrared thermal emitters because LEDs or LDs may generate remarkably less temperature variations inside the measurement cavity 15 compared to infrared thermal heating structures. Furthermore, compared to conventional thermal emitters, LEDs or LDs offer a much higher flexibility in their chopping frequency and would thus allow to exploit system resonances where the system is more sensitive than at lower frequencies and at the same time generates much less thermoacoustic signals. Thus, according to an exemplary embodiment, the emitter 10 does not comprise an infrared thermal emitter.

Even though the emitter 10 may comprise LEDs or LDs, the photoacoustic sensor 100 according to the present disclosure may comprise several advantages over common gas sensors relying on the scattering of light. For example, light scattering based sensors, such as nephelometers or particle counters may work fine for detecting particles having a size of 300 nm and more, but they will run into problems with decreasing PM-size. These conventional light scattering based devices also react to harmless particles like water droplets or salt crystals. Since water droplets and salt crystals may also scatter the light, they are detected as false positives. Furthermore, in common sensor devices that use heaters, the fan or pump used for cooling is the biggest component which limits the amount of downsizing.

According to some exemplary embodiments, the photoacoustic sensor 100 according to the present disclosure is fan-less. This allows a reduction in size of the photoacoustic sensor 100.

For example, the photoacoustic sensor 100 may comprise the measurements of a sugar cube. Accordingly, each of a length, a height and a width of the photoacoustic sensor 100 may be five centimeters or less. These measurements may be defined by the housing 31 of the photoacoustic sensor 100.

As can be seen in FIG. 3, at least the emitter 10 and the acoustic transducer 16 may be arranged inside the housing 31, wherein said housing 31 may also define the measurement cavity 15. The housing 31 may comprise a reflective coating on the inside.

According to some exemplary embodiments, the emitter 10 and the acoustic transducer 16 may both be arranged inside the same measurement cavity 15. The controller 101 may be arranged outside the housing 31, as shown in FIG. 3. Alternatively, the controller 101 may be arranged inside the housing 31. The photoacoustic sensor 100 may comprise at least one opening 32 for fluid communication with an environment such that the particulate matter 13 and the at least one target gas 14 can flow from the environment into the measurement cavity 15.

FIG. 3 shows an example, wherein at least one of the emitter 10, the acoustic transducer 16 and the controller 101 may be arranged on a common substrate 33, e.g., a PCB (Printed Circuit Board). The substrate 33 may comprise the above mentioned opening 32. Said opening 32 may be provided underneath the acoustic transducer 16. In other words, the opening 32 may be provided at a region of the substrate 33 foreseen for mounting the acoustic transducer 16.

Additionally or alternatively, the housing 31 may comprise an opening 34a being arranged on a top side 35 of the housing 31, i.e., on a side 35 opposite the substrate 33. Additionally or alternatively, the housing 31 may comprise an opening 34b being arranged on at least one of the lateral side walls 36 of the housing 31.

Irrespective of the location of the one or more openings 32, 34a, 34b, the photoacoustic sensor 100 may comprise a particulate filter for preventing at least a portion of the particulate matter 13 from entering into the measurement cavity 15, wherein the particulate filter may be arranged at the opening 32, 34a, 34b of the photoacoustic sensor 100.

The herein described concept allows to provide a photoacoustic sensor 100 being able to detect particulate matter having a size of less than 300 nm, while at the same time having a very small form factor of only a few centimeters.

Today's commonly known photoacoustic sensors instead comprise large form factors. For example, shoebox sized PAS lab- or stationary measurement equipment with optical path lengths of 10 cm and more have proven to be able to measure $NO_2$ concentrations to sub ppb (parts per billion) and soot particles <300 nm in concentrations that are relevant for measuring air quality, but to the best of the inventor's knowledge, a miniaturized (e.g., sugar cube size) PAS based module has never been proposed or shown so far, which is able to mutually detect particulate matter 13 and at least one target gas 14, preferably without using a thermal emitter.

Furthermore, while common gas sensors may use a quality factor Q of Q>15 or more, the photoacoustic sensor 100 according to the present disclosure may comprise a quality factor of Q<10 or even Q<6, which allows for a reduction in production costs. Still further, since the controller 101 may be configured to generate a combined signal 23, in which the quantity of the at least one target gas 14 may be corrected by the quantity of the particulate matter 13, it may be sufficient to measure the particulate matter 13 and/or the at least one target gas 14 in ppm (parts per million) in order to receive a valid result as to the concentration of the at least target gas 14 in the measurement cavity 15.

Figure 4:
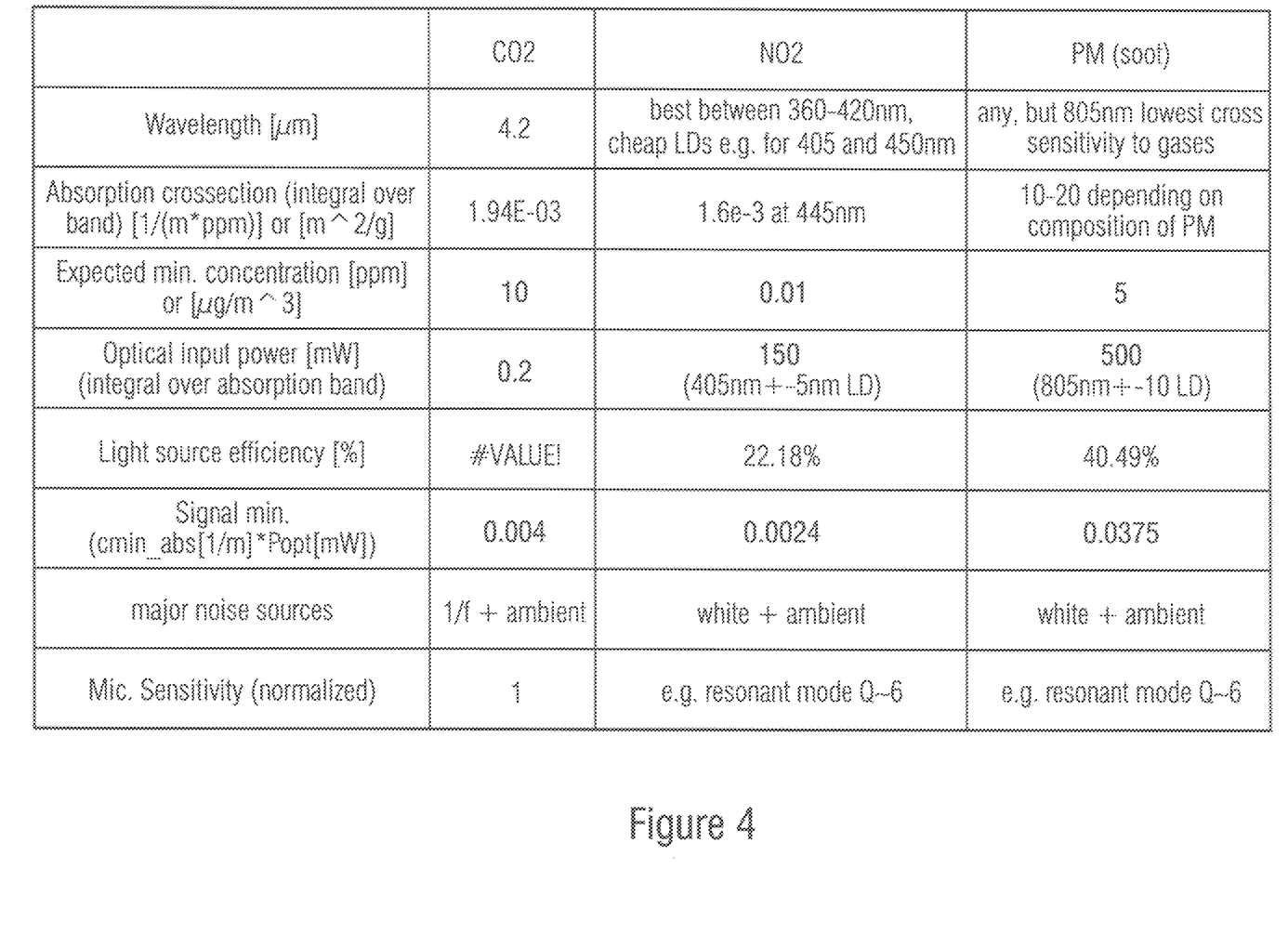
FIG. 4 shows a table presenting some exemplary figures for comparing a common $CO_2$ sensor with a photoacoustic sensor for detecting $NO_2$ and particulate matter according to an embodiment.

FIG. 4 shows a table 40 comprising some exemplary figures related with a photoacoustic sensor 100 according to the herein described principle. The second column 41 from left shows figures of a common CO 2 sensor. In comparison, the third and fourth columns 42, 43 from left show figures related with an example of a photoacoustic sensor 100 according to the present disclosure for mutually detecting $NO_2$ (third column), as an example of a target gas, and particulate matter (fourth column).

The figure of merit to be analyzed in this table 40 is the minimal signal that can be expected (sixth row 56). It is the product of absorption cross-section (second row 52), minimum concentration to be detected (fourth row 54) and available optical input power integrated over the absorption band (fifth row 55). Additionally, the acoustic transducer properties such as sensitivity and noise as well as bandwidth or Q-factor will further influence the resulting SNR (Signal to Noise Ratio) of the system and thus influence an achievable lower detection limit of the sensor 100. However, these may be very specific properties that may be optimized very carefully such that this table 40 may only represent some non-limiting examples. However, the fact that light sources like LEDs or LDs offer a much wider range of operation frequencies, compared to a thermal emitter, they offer the possibility to operate the system at resonances and thereby increase the SNR.

In summary, from the sixth row 56 it can be seen that ~1000 times lower minimum concentrations for $NO_2$ (ppb), compared to $CO_2$ (ppm), can be largely compensated by increasing the optical input power by three orders of magnitude, such that the figure of merit is comparable or slightly worse (factor 2) for $NO_2$ compared to $CO_2$. For PM the situation looks almost more relaxed but minimum expected concentrations may become less in upcoming PM1 or PM0.3 standards.

Figure 5:
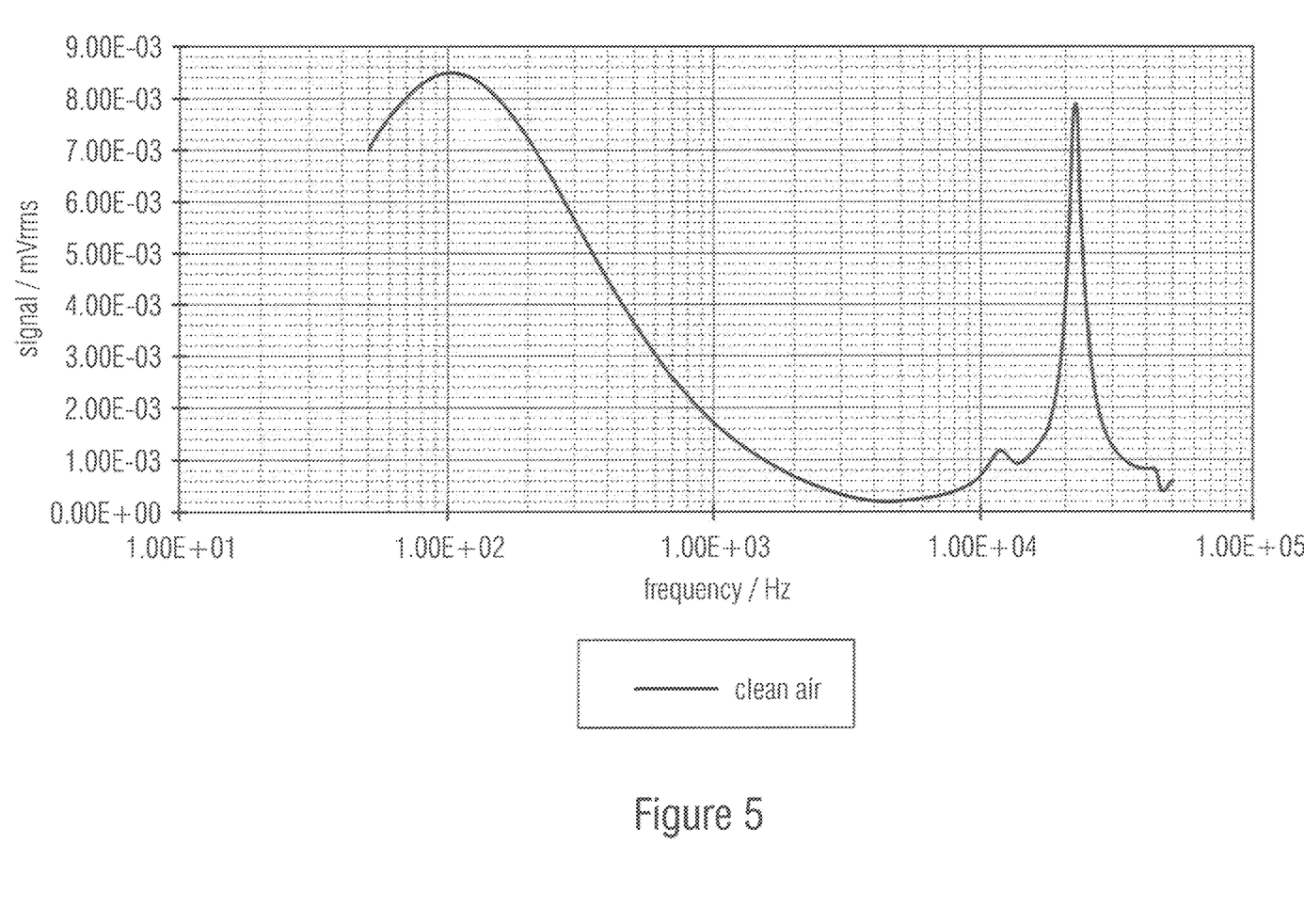
FIG. 5 shows a schematic diagram of an exemplary measurement executed with a photoacoustic sensor according to an embodiment.

FIG. 5 shows a diagram of a PAS measurement with a lock-in amplifier driven by a blue LD. It shows the capability of the LD to feed the system also at high resonances like the exemplary one in this non-limiting example at ~22 kHz, with a Q-factor of ~6. In a PAS system a careful trade-off design between operating frequency (the lower the frequency, the more PAS signal is excited) outside noise (here, a higher frequency is beneficial) and realistic lowest resonance frequency (this is mainly limited by system size) has to be done. But by using LEDs or LDs as light sources the design range may greatly be improved compared with thermal emitter light sources that show a very low frequency cut-off in their duty-cycle.

Some embodiments according to the herein described principle suggest using a LED or LD light source in combination with a miniaturized PAS module in order to measure relevant gas properties for AQI such as e.g.

1.) $NO_2$ (wavelength: e.g., 405 nm);

2.) PM (wavelength: e.g., 805 nm or 850 nm); and whereby it is possible to have either individual modules for each component or several light sources in one module in order to provide a multi gas/PM sensor module.

The photoacoustic sensor 100 according to this disclosure and advantages being related with said photoacoustic sensor 100 shall be briefly summarized in the following bullet points:

- Usage of LED or LD light sources to measure gases like e.g., $NO_2$ and also PM;
- Compared to a slow thermal emitter used in common PAS modules, LEDs and LDs will allow to exploit system resonances at higher frequencies to boost sensitivity of the system;
- Not sensitive to water droplets or salt crystals (false negatives);
- Avoid fan or pump and go directly for PM1 or PM0.3 where it may be possible to rely on diffusion only instead of convection using pumps;
- Possibility to extrapolate PM2.5 based on PM1 result;
- Less drift than chemical sensors at reasonably small form factor;
- possibility to offer compact combo sensors like $NO_2$ and PM in one module PM PAS has the potential to be chemistry selective (measures only black soot and not water droplets or salt crystals) and capable to measure really fine particles of <300 nm.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While this disclosure has been described with reference to illustrative embodiments, this description is not intended to be construed in a limiting sense. Various modifications and combinations of the illustrative embodiments, as well as other embodiments of this disclosure, will be apparent to persons skilled in the art upon reference to the description. It is therefore intended that the appended claims encompass any such modifications or embodiments.

What is claimed is:

1. A photoacoustic sensor comprising:

an emitter comprising a first emitter element for emitting optical radiation at a first wavelength and a second emitter element for emitting optical radiation at a second wavelength different from the first wavelength, wherein the emitter comprises at least one of a light emitting diode or a laser diode, wherein the first wavelength is for photoacoustically detecting particulate matter in a single measurement cavity and the second wavelength is for photoacoustically detecting the particulate matter and at least one target gas in the single measurement cavity; and an acoustic transducer comprising a microelectromechanical (MEMS) microphone for transducing a first acoustic signal into a first sensor signal depending on an interaction of the optical radiation at the first wavelength and the particulate matter, and for transducing a second acoustic signal into a second sensor signal depending on an interaction of the optical radiation at the second wavelength with the particulate matter and the at least one target gas; and a controller configured to determine a quantity of the particulate matter inside the measurement cavity based on the first sensor signal and to determine a mutual quantity of the particulate matter and the at least one target gas inside the measurement cavity based on the second sensor signal, wherein the photoacoustic sensor comprises a housing that defines the measurement cavity, and at least the emitter and the acoustic transducer are arranged inside the housing, wherein the first emitter element and the second emitter element are arranged on a common substrate, wherein the acoustic transducer and the controller are arranged on the common substrate, wherein the housing is affixed to the common substrate, and wherein the common substrate comprises a single printed circuit board.

2. The photoacoustic sensor of claim 1, wherein the controller is further configured to determine a quantity of the at least one target gas inside the measurement cavity based on a combination of the first and second sensor signals.

3. The photoacoustic sensor of claim 1, wherein the emitter is tunable through a wavelength spectrum covering the first and second wavelengths.

4. The photoacoustic sensor of claim 1, wherein the emitter does not comprise an infrared thermal emitter.

5. The photoacoustic sensor of claim 1, wherein the at least one target gas is a gas belonging to a family of nitrogen oxides.

6. The photoacoustic sensor of claim 1, wherein the first wavelength is in a range between 600 nm and 1100 nm, and wherein the second wavelength is in a range between 200 nm and 600 nm, or wherein the first wavelength is 805 nm±10 nm or 850 nm±10 nm, and wherein the second wavelength is 405 nm±5 nm or 450 nm±5 nm.

7. The photoacoustic sensor of claim 1, wherein the photoacoustic sensor is configured to detect particulate matter with dimensions of 300 nm and less.

8. The photoacoustic sensor of claim 1, wherein each of a length, a height and a width of the photoacoustic sensor is five centimeters or less.

9. The photoacoustic sensor of claim 1, wherein the photoacoustic sensor is fan-less.

10. The photoacoustic sensor of claim 1, wherein the photoacoustic sensor comprises at least one opening for fluid communication with an environment such that the particulate matter and the at least one target gas can flow from the environment into the measurement cavity.

11. The photoacoustic sensor of claim 10, wherein the photoacoustic sensor further comprises a particulate filter for preventing at least a portion of the particulate matter from entering into the measurement cavity, the particulate filter being arranged at the opening of the photoacoustic sensor.

12. The photoacoustic sensor of claim 1, wherein the first emitter element comprises a red Light Emitting Diode or a red Laser Diode, and wherein the second emitter element comprises a blue Light Emitting Diode or a blue Laser Diode.

13. A photoacoustic sensing method, the method comprising:

emitting electromagnetic radiation at a first wavelength and electromagnetic radiation at a second wavelength, wherein the first wavelength is for photoacoustically detecting particulate matter in only a single measurement cavity and the second wavelength is for photoacoustically detecting the particulate matter and at least one target gas in only the single measurement cavity; and transducing a first acoustic signal into a first sensor signal depending on an interaction of the electromagnetic radiation at the first wavelength and the particulate matter, and for transducing a second acoustic signal into a second sensor signal depending on an interaction of the electromagnetic radiation at the second wavelength with the particulate matter and the at least one target gas; and determining a quantity of the particulate matter inside the single measurement cavity based on the first sensor signal and determining a mutual quantity of the particulate matter and the at least one target gas inside the single measurement cavity based on the second sensor signal, wherein emitting electromagnetic radiation at the first wavelength and electromagnetic radiation at the second wavelength is performed by an emitter arranged inside a housing defining the single measurement cavity, wherein determining the quantity of the particulate matter and the mutual quantity of the particulate matter and the at least one target gas is performed by a controller, wherein transducing the first acoustic and the second acoustic signal is performed by an acoustic transducer arranged in the housing defining the single measurement cavity, wherein the emitter comprises a first emitter element and a second emitter element arranged on a common substrate, wherein the housing, the acoustic transducer, and the controller are affixed to the common substrate, and wherein the common substrate comprises a single printed circuit board.

* * * * *